United States Patent
Sauter

(10) Patent No.: US 6,943,260 B2
(45) Date of Patent: Sep. 13, 2005

(54) PROCESS FOR OBTAINING BETULINIC ACID

(75) Inventor: Markus Sauter, Gensingen (DE)

(73) Assignee: Boehringer Ingelheim Pharma GmbH & Co. KG, Ingelheim (DE)

(*) Notice: Subject to any disclaimer, the term of this patent is extended or adjusted under 35 U.S.C. 154(b) by 275 days.

(21) Appl. No.: 10/355,806

(22) Filed: Jan. 31, 2003

(65) Prior Publication Data

US 2003/0149286 A1 Aug. 7, 2003

Related U.S. Application Data

(60) Provisional application No. 60/386,336, filed on Jun. 6, 2002.

(30) Foreign Application Priority Data

Feb. 2, 2002 (DE) .......................... 102 04 271

(51) Int. Cl.⁷ ............................... C07J 53/00
(52) U.S. Cl. ..................................... 552/510
(58) Field of Search ........................... 552/510

(56) References Cited

U.S. PATENT DOCUMENTS 6,175,035 B1  1/2001  Draeger et al.
6,264,998 B1  7/2001  Ramadoss et al.
6,569,842 B2 * 5/2003  Pezzuto et al. ............. 514/169

FOREIGN PATENT DOCUMENTS

JP   356057780 A  *  5/1981
WO   WO-0110885 A3    2/2001
WO   WO-0110885 A2    2/2001

OTHER PUBLICATIONS

Bruckner et al., "Occurrence of Betulinic Acid in the Bark of the Plane Tree." J. Chem. Soc., (181), pp. 948–951, 1948.*

V. Bruckner et al; "Occurence of Betulinic Acid in the Bark of the Plane Tree"; J. Chem Soc. (1948) No. 181; pp. 948–951.

Robertson, A. et al; Polyterpenoid Compounds. Part. I. Betulic Acid from Comus florida, L.; Journal of Chemical Society; 1939; pp. 1267–1273.

* cited by examiner

*Primary Examiner*—Barbara P. Badio
(74) *Attorney, Agent, or Firm*—Michael Morris; Mary-Ellen M. Devlin; David A. Dow

(57) ABSTRACT

The invention relates to an improved process for obtaining highly pure, crystalline betulinic acid from a methanolic extract of ground plane tree cortex and/or plane tree bark, as well as highly pure crystalline betulinic acid which is solvated with one equivalent of ethanol.

12 Claims, No Drawings

PROCESS FOR OBTAINING BETULINIC ACID

RELATED APPLICATIONS

Benefit of U.S. Provisional Application Ser. No. 60/386,336, filed on Jun. 6, 2002 is hereby claimed, and said Application is herein incorporated by reference.

DESCRIPTION

The invention relates to an improved process for obtaining highly pure, crystalline betulinic acid from a methanolic extract of ground plane bark.

BACKGROUND TO THE INVENTION

Betulinic acid is 3β-hydroxy-lup-20(29)-ene-28-acid of formula

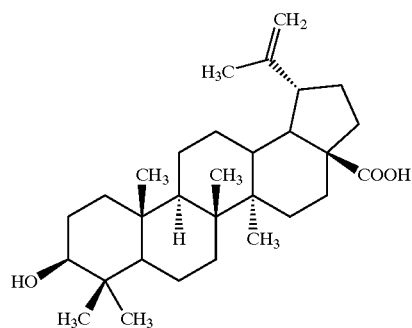

It is known that betulinic acid is effective against the growth of melanoma cells (e.g. Pisha et al., Nature Medicine 1, 1995, 1046 ff) as well as against other cancer cells (e.g. Sunder et al., U.S. Pat. No. 6,048,847). In addition its amides are supposed to be suitable for use against HIV (e.g. Evers et al., J. Med. Chem. 39, 1996, 1056 ff; or Soler et al., J. Med. Chem. 39, 1996, 1069 ff). Consequently betulinic acid is in great demand.

Apart from being produced synthetically (e.g. L. Ruzicka et al., Helv. Chim. Acta 21, 1938, 1076 ff) betulinic acid may also be obtained from various plants, particularly trees, such as for example from the outer bark or cortex of *Picramnia pentandra* (e.g. Herz et al., Phytochemistry 11, 1972, 3061 ff), from the cortex of *Arbutus menziesii* (Robinson et al., Phytochemistry 9, 1970, 907 ff) and from the cortex of *Ziziphus mauritiana* (e.g. Pisha et al., Nature Medicine 1, 1995, 1046 ff).

It is difficult to isolate betulinic acid from these starting materials. By contrast it would appear more promising to obtain it from the cortex and/or bark of the plane tree (*Platanus acerifolia*). DE 197 13 768 proposes a process for obtaining betulinic acid, in which a powder obtained from plane bark is extracted with a medium polarity solvent such as for example dichloromethane, chloroform or diethyl ether.

However, this process is unsuitable for the industrial recovery of large amounts of betulinic acid, as very large volumes of the medium polarity solvent have to be used to extract the betulinic acid (7 litres of dichloromethane are used to 150 g of powdered plane tree bark).

Bruckner et al., J. Chem. Soc. 1948, 948–951 describe a process for obtaining betulinic acid from plane bark in which the ground bark is extracted with methanol, the extract obtained is evaporated down, and the concentrate is repeatedly recrystallised from methanol in the presence of charcoal. However, the betulinic acid thus obtained still contains a large number of impurities.

The aim of the present invention was therefore to provide an improved process for the large-scale recovery of highly pure, crystalline betulinic acid from plane bark and/or plane tree cortex which avoids the disadvantages of the known methods.

DETAILED DESCRIPTION OF THE INVENTION

Surprisingly it has now been found that highly pure crystalline betulinic acid can be obtained from a methanolic extract of ground plane bark and/or plane cortex by evaporating the extract down and crystallising it from an alcohol if the residue from the methanolic extraction is washed with a nonpolar diluent before the crystallisation.

The present invention thus relates to a process for obtaining highly pure, crystalline betulinic acid from a methanolic extract of ground plane bark and/or plane cortex by evaporation of the extract and crystallisation from an alcohol, characterised in that before the crystallisation the residue is washed with a nonpolar diluent.

The term "betulinic acid" as used above and hereinafter includes both betulinic acid as such and the hydrates and solvates thereof, preferably betulinic acid, which is solvated with 1 to 2 equivalents of an alcohol, particularly one equivalent of ethanol.

The invention further relates to highly pure crystalline betulinic acid which is solvated with one equivalent of ethanol.

The Western plane tree (*Platanus occidentalis*) has proved particularly suitable as the plane tree in question.

Suitable alcohols for recrystallising the crude betulinic acid are generally aliphatic alcohols with 1 to 4 C-atoms, particularly methanol, ethanol or isopropanol or mixtures thereof, most preferably ethanol.

Suitable nonpolar diluents are generally aliphatic, cycloaliphatic or aromatic hydrocarbons or mixtures thereof, preferably aliphatic hydrocarbons with 5 to 8 carbon atoms, particularly pentane, hexane or heptane, most preferably n-hexane, cycloaliphatic hydrocarbons with 5 to 8 carbon atoms, particularly cyclopentane, cyclohexane, methylcyclohexane, or aromatic hydrocarbons with 6 to 9 carbon atoms, particularly toluene or xylene.

Preferred embodiments of the invention are:

(A) a process for obtaining betulinic acid comprised of the steps of washing and isolating the residue of a methanolic extract are carried out successively:
  (i) heating the residue in a nonpolar diluent;
  (ii) separating the residue from the diluent;
  (iii) heating the residue in ethanol, clarifying the ethanolic phase by the addition of activated charcoal and separating the activated charcoal from the ethanolic phase at a temperature between 60 and 95° C.; and
  (iv) crystallising and separating the betulinic acid from the ethanolic phase.

(B) processes in which the ground plane cortex is heated to boiling with 2 to 5 times the amount of methanol for 0.5 to 5.0 hours, extracted, the extract obtained is filtered at a temperature between 40 and 60° C., evaporated down to 30 to 70% of its volume and crystallised at a temperature between −10 and +10° C.

(C) processes in which the residue of the methanolic extract is taken up in 2 to 8 times the amount of an aliphatic hydrocarbon, preferably cyclohexane, methylcyclohexane or n-hexane, particularly n-hexane, and the mixture is heated to boiling.
(D) processes in which in step (ii) the residue is separated from the diluent by centrifuging or suction filtering.
(E) processes in which in step (iii) the residue is taken up in 20 to 100 times, preferably 30 to 80 times, particularly 40 to 60 times the amount of ethanol and heated to boiling.
(F) processes in which in step (iv) the ethanolic phase is cooled to temperatures of −10 to +10° C., preferably 0 to +5° C., the betulinic acid precipitated is separated off by centrifuging or suction filtering and dried.
(G) processes in which the betulinic acid obtained is in the form of the monoethoxide.

Highly pure crystalline betulinic acid which is solvated with one equivalent of ethanol is particularly preferred, particularly the betulinic acid ethoxide of formula

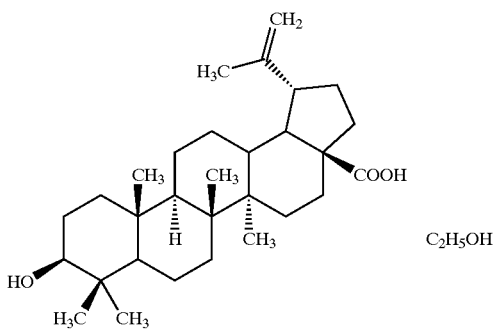

In a most particularly preferred embodiment of the process according to the invention the powdered plane cortex is suspended in 2 to 5 times, preferably 3 to 4 times as much methanol and heated for 1 to 5 hours, particularly about 2 hours, preferably by refluxing. The suspension is filtered at 40 to 60° C., particularly at about 50° C., the methanol extract is evaporated down to 60 to 40%, particularly about 50% of its volume. The concentrated extract is cooled to 0 to 10° C., particularly about 5° C., filtered off and washed with cold methanol. The residue is preferably dried in vacuo at 40 to 70° C., particularly at about 50° C.

In this way, the crude betulinic acid is obtained as a colorless powder (about 2.0 to 2.5%, based on plane cortex). This is suspended in 4 to 8 times, particularly 5 to 6 times as much n-hexane, cyclohexane or methylcyclohexane and heated for 0.5 to 2 hours, particularly 1 hour, particularly by refluxing. In the event that hereinabove or hereinbelow the relation of two compounds is indicated in the form of "x to y fold amount of the first compound", wherein x and y represent the lower and upper limit of said amount, this indication relates to "x to y " parts per weight of said first compound with respect to 1 part per weight of the second compound. The suspension obtained is centrifuged or suction filtered, washed with 1.5 to 4.5 times, particularly about 3 times as much hot n-hexane, cyclohexane or methylcyclohexane, and the residue is dried overnight at about 40° C., preferably in vacuo.

The betulinic acid thus obtained is dissolved in 30 to 50 times as much ethanol, with heating. Activated charcoal is added and the mixture is filtered while hot. As it cools, crystallisation begins. The mixture is cooled to 0 to 10° C., particularly 5° C., suction filtered or centrifuged and washed with cold ethanol.

Highly pure crystalline betulinic acid is obtained, which is solvated with one mol of ethanol.

The following Example serves to illustrate a process for obtaining betulinic acid which is carried out by way of example. It is intended solely as a possible procedure provided as an illustration, without restricting the invention to its contents.

EXAMPLE
1A Extraction of the Plane Cortex
4500 g of plane cortex powder (ground in a cutter mill) are suspended in 15 l of methanol and refluxed for 2 h. The suspension is filtered at about 50° C., the methanol extract is evaporated down to 50% of its volume (7.5 l). The concentrated extract is cooled to 5° C., filtered off and washed with 2 l of cold methanol. The residue is dried in vacuo at 50° C.
104 g of crude betulinic acid are obtained as a colourless powder (2.3%, based on plane tree cortex). HPLC: 90.6%
1B Stirring out from Nonpolar Solvent
93 g of betulinic acid obtained according to Example 1A are suspended in 600 ml of n-hexane and refluxed for 1 hour. The suspension is suction filtered through a nutsche, washed with 300 ml of hot n-hexane, and the residue is dried overnight at 40° C. in vacuo. 89.5 g (96.2%) of betulinic acid are obtained as a colourless powder. HPLC: 94.75%
Cyclohexane, methylcyclohexane or mixtures of these solvents may also be used analogously.
1C Recrystallisation from Ethanol
89 g of betulinic acid obtained according to Example 1B are refluxed and dissolved in 4 l of ethanol. 40 g of activated charcoal are added and the mixture is filtered hot through a nutsche. After cooling to ambient temperature, crystallisation sets in. The mixture is cooled to 5° C., suction filtered and washed with 500 ml of cold ethanol. 63.5 g (71.3%) of crystalline betulinic acid is obtained, which is solvated with 1 mol of ethanol. HPLC: 93.8% (percentage area 100%); melting point=296–298° C., $[\alpha]D = +8$, c=0.9 in pyridine.
1D Working up the Mother Liquor
4 l of the ethanolic mother and washing liquor from Example 1C are evaporated down to 1 litre in vacuo, suction filtered at 5° C. and washed with cold ethanol. 20 g (22.5%) of betulinic acid are obtained. HPLC: 96.5%

We claim:
1. A process for obtaining highly pure, crystalline betulinic acid from a methanolic extract of ground plane tree cortex and/or plane tree bark comprising the steps of:
  i) concentrating said methanolic extract to provide a residue;
  ii) heating the residue in a non-polar diluent;
  iii) separating the residue from the diluent;
  iv) heating the residue in ethanol and providing an ethanolic phase;
  v) clarifying said ethanolic phase by adding activated charcoal and separating said activated charcoal from said ethanolic phase at a temperature between 60 and 95° C.; and
  (vi) crystallising and separating betulinic acid from said ethanolic phase.
2. The process of claim 1, wherein steps (ii)–(vi) are performed in the order recited.
3. Process according to claim 1, wherein the methanolic extract is prepared by heating the ground plane tree cortex to boiling with 2 to 5 times the amount of methanol for 0.5 to 5.0 hour, and then filtering the extract obtained at a temperature between 40 and 60° C., and then evaporating the filtrate down to 30 to 70% of its volume and crystallizing at a temperature between −10 and +10° C.
4. Process according to claim 1, wherein said residue of said methanolic extract is taken up in 2 to 8 times the amount of non polar diluent and the mixture is heated to boiling.
5. The process of claim 4, wherein the aliphatic hydrocarbon is selected from the list consisting of cyclohexane, methylcyclohexane and n-hexane.

6. Process according to claim 1, wherein said residue in step (iii) is separated from said diluent by centrifuging.

7. Process according to claim 1, wherein said residue in step (iv) is taken up in 20 to 100 times the amount of ethanol and heated to boiling.

8. Process according to claim 1, wherein said ethanolic phase of step (v) is cooled to temperatures of −10 to +10° C., and the betulinic acid precipitated is separated off by centrifuging and then dried.

9. Process according to claim 1, wherein said ethanolic phase of step (v) is cooled to temperatures of 0 to 5° C. and the betulinic acid precipitated —is separated of —by centrifuging and then dried.

10. Process according to claim 1, wherein the betulinic acid thus obtained is present as the monoethoxide.

11. A highly pure crystalline betulinic acid made by the process of claim 1 wherein said beulinic acid is solvated with one equivalent of ethanol.

12. A highly pure crystalline betulinic acid according to claim 11 of formula

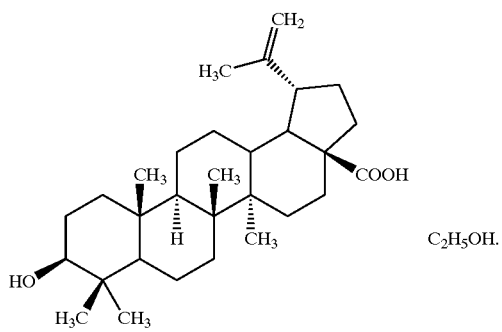

C₂H₅OH.

* * * * *